(12) United States Patent
Rees

(10) Patent No.: US 6,946,241 B2
(45) Date of Patent: Sep. 20, 2005

(54) PHYSIOLOGICAL MEDIUM FOR PERFUSING, PRESERVING AND STORING ISOLATED CELL, TISSUE AND ORGAN SAMPLES

(75) Inventor: Douglas Rees, London (GB)

(73) Assignee: Res-Del International Limited, Oxfordshire (GB)

( * ) Notice: Subject to any disclaimer, the term of this patent is extended or adjusted under 35 U.S.C. 154(b) by 182 days.

(21) Appl. No.: 09/936,878

(22) PCT Filed: Jan. 22, 2001

(86) PCT No.: PCT/GB01/00241

§ 371 (c)(1),
(2), (4) Date: Sep. 3, 2002

(87) PCT Pub. No.: WO01/52647

PCT Pub. Date: Jul. 26, 2001

(65) Prior Publication Data

US 2003/0077655 A1 Apr. 24, 2003

(30) Foreign Application Priority Data

Jan. 20, 2000 (GB) .............................................. 0001172

(51) Int. Cl.[7] .............................. A01N 1/00; A01N 1/02; C12N 5/00
(52) U.S. Cl. .......................... 435/1.1; 435/1.2; 435/1.3; 435/2; 435/406
(58) Field of Search .......................... 435/1.1, 1.2, 1.3, 435/2, 406

(56) References Cited

PUBLICATIONS

Parr et al., "Interaction between betamethasone and vecuronium", Brithish Journal of Anaesthesia 67 : 447–451 (1991).*
Clements et al., "Preservation of inherent contractility in isolated gut segments from herbivorous and carnivorous marine fish", Comp. Physiol. B, 168:61–72 (1998).*
Gibco BRL Catalogue, p. 72, 1992.*
Rees et al., "Effect of RES–DEL RS–C solution on the viability of isolated rat heart preparations over 1–6 hours of cardioplegic arrest", Proceeding of the Physiological Society of New Zealand 14 :19 (1995).*
Rees, Proceedings of the Physiological Society, Feb. 1978, 278, 8–9P.
Rees (1989) Isolated Perfused Organ Preparatoins. Eds. H.J. Doring, H. Dehnert, Biomesstechnik–Verlag March GmbH, vol. 5 pp. 85–94 and pp. 123–132.
Proceedings of the Physiological Society of New Zealand vol. 14 Aug 1995—Abstracts of two articles one by Rees, and one by Rees and Clissold.
Clements and Rees, J Comp Physiol B (1998) 168: 61–72—Preservation of Inherent Contractllity in Isolated Gut Segments from Herbivorous and Carnivorous Marine Fish.
Andrews, Ainswoth and Abernethy—Transactions of the Royal Society of Tropical Medicine and Hygiene (1994) 88, 200–203.
Parr, Robinson, Rees and Galletly—British Journal of Anaesthesia 1991: 67, 447–451 Interaction Between Betamethasone and Vecuronium.

* cited by examiner

Primary Examiner—Sandra E. Saucier
(74) Attorney, Agent, or Firm—Thompson Coburn LLP

(57) ABSTRACT

A physiological liquid medium is provided having the basic, synergistic components to allow its universal application in preserving cellular and functional integrity in vitro of different cell, tissue and organ types isolated from different mammalian species. The medium comprises an aqueous solution in sterile purified water of: i) a salt component comprising: a) from 100 to 150 mmoles/L of sodium ions, b) from 2.5 to 6.2 mmoles/L of potassium ions, c) from 1.0 to 2.5 mmoles/L of calcium ions, d) from 0.4 to 25 mmoles/L of magnesium ions, and e) from 96 to 126 mmoles/L of chloride ions; ii) a buffer component comprising: f) from 21 to 27 mmoles/L of bicarbonate ions, and g) from 1 to 12 mmoles/L of TES, MOPS or BES; iii) a substrate component comprising: h) 2 to 11 mmoles/L of glucose, I) 50 to 150 $\mu$moles/L of glycerol and j)7 zo 15 $\mu$moles/L of choline; iv) an amino acid component comprising: k) 5 to 400 $\mu$moles/L of glutamate, 1) 5 to 200 $\mu$moles/L of aspartate and m) 100 to 2000 $\mu$moles/L of glutamine; v) a co-enzyme component comprising: n) 1 to 120 nmoles/L of thiamine cocarboxylase; vi) a vitaminoid component comprising: o) 40 to 70 $\mu$moles/l of D- or DL- or L-carnitine; vii) a protein component comprising: p) 5 to 200 m I.U./L of porcine or human insulin.

15 Claims, 4 Drawing Sheets

Figure 1:
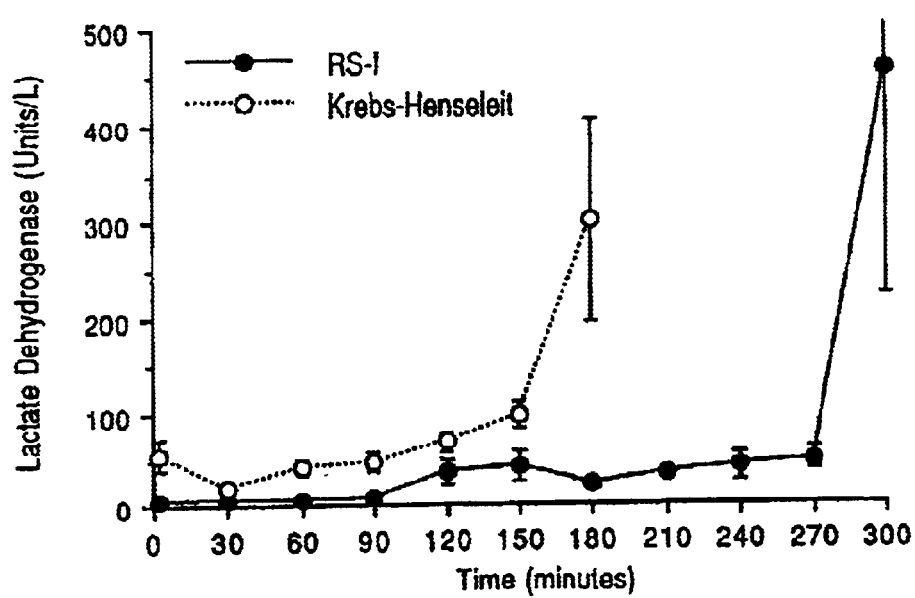

Analysis of Tetanic Fade Responses over Experimental Time

PHYSIOLOGICAL MEDIUM FOR PERFUSING, PRESERVING AND STORING ISOLATED CELL, TISSUE AND ORGAN SAMPLES

The present invention relates to the formulation of a physiological liquid medium having the basic, synergistic components to allow its universal application in preserving cellular and functional integrity in vitro of different cell, tissue and organ types isolated from different mammalian species.

Historically, the design of physiological perfusion solutions dates back to the thesis proposed by the French physiologist, Claude Bernard in the eighteen seventies who put forward his theory on the milieu intériéur, basically purporting that to maintain the whole (person) one should ensure that the surrounding extracellular environment should be balanced in all respects. Unfortunately, the misinterpretation or misconception of Bernard's milieu intériéur has led researchers to confuse the extracellular with the intracellular phases of cell function and largely to overlook the need to maintain the cell as a whole entity. The basic salt solutions currently used for in vitro or isolated organ/tissue studies derive from the simple formulation used by Sidney Ringer for the isolated perfused frog heart. Similar, empirically contrived, basic salt solutions have been utilised for isolated mammalian preparations. The conventional use of phosphate/bicarbonate buffered salines was instigated by Krebs and Henseleit (Z. Physiol. Chem. 210: 33–66) for studies on isolated homogenates of mitochondria, ie. intracellular organelles, from pigeon liver. Later, Krebs, in his classical paper (Biochem. Biophys. Acta. 4: 249–269) on the analysis of oxygen consumption in tissue slices from different organs in a variety of animal species, acknowledged that substrate depletion in isolated tissue/organ preparations over time was a consideration that had not been addressed in the composition of previous physiological solutions. As has already been demonstrated, a correct interpretation of Bernard's hypothesis necessitates that the whole cell should subtend metabolic homeostasis. Traditionally, phosphate/bicarbonate buffers have been used for sixty years and are still currently used, with questionable validity, in perfusion/preservation solutions for mammalian and human tissues/organs. It is of interest to note that it has been known for 40 years that inorganic phosphate ions inhibit glycolysis and oxidative phosphorylation, creatine kinase and the enzymes involved in oxygen free radical scavenging, the latter being implicated in reperfusion injury and oedema formation in numerous organ systems. Maintenance of pH over time is further complicated by the instability of phosphate-buffered perfusion and preservation solutions caused by the precipitation of calcium phosphate and bicarbonate, accentuated by the change in their dissociation constants over the temperature range 4–37° C.

GB-A-2 270 614 describes an aqueous solution for the perfusion, storage and reperfusion of organs comprising calcium, potassium and magnesium chlorides, histidine, mannitol, lactiobionate, glutamate and glutathione.

GB-A-2 213 362 discloses a perfusate solution which comprises a lactobionate and a hydroxyethyl starch. The descriptive section of that document stresses the importance of including an adenosine triphosphate (ATP) precursor such as adenosine, in order to maintain the ATP level during reperfusion.

WO 98/04127 discloses a transplant solution comprising water, a buffer system and pyruvate.

The present invention provides an answer to the still-existing need to provide a solution to overcome the deleterious effects of inorganic phosphate ions on cell metabolism and associated cellular function while also serving to augment the natural physiological processes essential to preservation of isolated cell, tissue and organs from mammalian species, for instance during the transport of organs for transplant. Such organs deteriorate rapidly, and many useful organs cannot be used because too much time elapses between collection and delivery to an intended recipient. The solution according to the present invention extends the safe period.

The present invention provides a physiological medium which comprises an aqueous solution in sterile purified water of:

(i) a salt component comprising:
   (a) from 100 to 150 mmoles/L of sodium ions,
   (b) from 2.5 to 6.2 mmoles/L of potassium ions,
   (c) from 0.1 (preferably from 0.15) to 2.5 mmoles/L of calcium ions,
   (d) from 0.4 to 25 mmoles/L of magnesium ions, and
   (e) from 96 to 126 mmoles/L of chloride ions;

(ii) a buffer component comprising
   (f) from 21 to 27 mmoles/L of bicarbonate ions, and
   (g) from 1 to 12 mmoles/L of TES, MOPS or BES;

(iii) a substrate component comprising:
   (h) 2 to 11 mmoles/L of glucose
   (i) 50 to 150 $\mu$moles/L of glycerol and
   (j) 7 to 15 $\mu$moles/L of choline;

(iv) an amino acid component comprising:
   (k) 5 to 400 $\mu$moles/L of glutamate
   (l) 5 to 200 $\mu$moles/L of aspartate and
   (m) 100 to 2000 $\mu$moles/L of glutamine;

(v) a co-enzyme component comprising:
   (n) 1 to 120 nmoles/L of thiamine cocarboxylase;

(vi) a vitaminoid component comprising:
   (o) 40 to 70 $\mu$moles/L of D- or DL- or L-carnitine;

(vii) a protein component comprising:
   (p) 5 to 200 m I.U./L of porcine or human insulin.

According to one embodiment, the salt component comprises
   (c) from 1.0 to 2.5 mmoles/L of calcium ions, and
   (d) from 0.4 to 2.4 mmoles/L of magnesium ions.

The present invention also provides a method for producing a physiological medium as described above which comprises adding in the following order: sodium chloride, potassium chloride, calcium chloride, magnesium chloride, the TES, MOPS, or BES, thiamine, carnitine, choline, glycerol, insulin, aspartate, glucose, glutamate, glutamine, and sodium bicarbonate to sterile purified water, with constant stirring, making up to the desired volume, filtering and storing in sterile sealed vessels.

It will be noted that the compositions according to the invention contain no animal derived serum protein, such as foetal bovine serum or bovine serum albumin, which have been banned by the FDA for such applications in single cell or human tissue/organ biotechnology.

Buffer Components:

With regard to the components of the solutions according to the invention a natural physiological buffer system, namely $NaHCO_3/pCO_2$, has been adopted for the solution in accordance with the invention, in combination with the zwitterionic Good's buffer, BES (Good et al. Biochemistry 5: 467–477), which acts by virtue of its ideal $pK_a$ over a temperature range of 10–37° C., to provide a stable pH, an essential requisite for cellular preservation. BES has been shown to be non-toxic to even cultured mammalian cells in long-term studies and exhibits negligible binding of $Ca^{2+}$ or $Mg^{2+}$, so removing the potential hazard of precipitation of divalent ions which occurs when using conventional bicarbonate/phosphate or double phosphate buffer solutions. Indeed, 10×concentrates of solutions according to the invention have been experimentally shown to have a shelf-life (stored at 3–8° C.) in excess of 14 months. As alternatives to the use of N,N-bis-(2-hydroxyethyl)-2-amino ethanesulfonic acid (BES), it is possible to use morpholinopropane sulfonic acid (MOPS) or N-tris-hydroxymethyl) methyl-2-amino ethanesulfonic acid (TES).

A major distinguishing feature of solution in accordance with the invention in comparison to conventional perfusion salines is the absence of inorganic phosphate which, for the past 80 years, has been used as the buffer vehicle in conventional perfusion solutions, even though inorganic phosphate radicals have been shown over the last 40 years to inhibit glycolysis and oxidative phosphorylation, creatine kinase activity, and free radical scavenging enzymes.

Inorganic phosphate has been reported to have an inhibitory effect on glycolysis by interfering with the co-operativity of $Mg^{2+}$ with the rate limiting enzymes, hexokinase and phosphofructokinase, and on the solubility of creatine kinase. Numerous investigators, in an attempt to compensate for the inhibitory effect upon glycolysis and associated decline in physiological performance produced by phosphate buffered salines, have included pyruvate at non-physiological serum levels (i.e. 2.0–25.0 mmoles vs 0.2 mmoles) in their perfusate salines or to transplant solutions (see the above-mentioned WO 98/04127). Experiments conducted on the isolated, perfused/perifused rat liver have shown that leakage of lactate dehydrogenase (LDH) occurred after only 10 minutes with Krebs & Henseleit saline but not for 300 minutes with a solution in accordance with the invention (see Example 1). Under the latter conditions, the further addition of pyruvate would be contraindicated as pyruvate is known to cause inhibition of the $H_4$ and $H_3M$ subunits of LDH in the liver and, incidentally, the heart. Again, it may be emphasised that for the preservation of isolated tissues/organs, all attempts should be made to retain metabolic homeostasis at the cellular level by maintaining 'autoregulation' of enzymatic function.

The preferred salt component comprises:
135.32 mmoles/L of sodium ions, 5.00 mmoles/L of potassium ions, 1.25 mmoles/L of calcium ions, 0.45 mmoles/L of magnesium ions, as chloride salts, and 118.40 mmoles/L of chloride ions as sodium, potassium, calcium and magnesium salts.

The preferred buffer component comprises:
25.00 mmoles/L of bicarbonate ions as sodium salt and 5.0 mmoles/L of N,N-bis(2-hydroxy ethyl)-2-amino-ethanesulfonic acid (BES).

Substrate Components

The solution according to the invention provides a number of essential substrates to retain metabolic homeostasis of the isolated organs/tissues. Glucose and glycerol have been shown to be satisfactory in meeting the energy demands of isolated tissues and organs, even when they are not the preferred substrate for the organ (e.g. the heart) by the inclusion of physiological levels of insulin. Apart from their ability to be metabolised, glycerol and glucose also have free radical scavenging and membrane stabilizing properties, which have been shown to be extremely important in maintaining the physiological viability of isolated tissues and organs. Preferably, the substrate component comprises 10 mmoles/L of D-glucose, 110 μmoles/L of glycerol and 10.0 μmoles/L of choline as the chloride salt.

Amino Acid Components:

Aspartate and glutamate have also been included in solutions according to the invention to enhance oxidative metabolism by replenishing TCA cycle intermediates, thereby maintaining high energy phosphate levels even during ischemic insult. Similarly, glutamate is involved in maintaining intracellular oxidation-reduction potentials. Essentially, it is suggested that, by optimising the aspartate-malate and glycerol phosphate shuttles, cells will maintain an optimal NAD/NADH balance and thereby sustain adenine nucleotide levels.

Preferably, the amino acid component comprises 300 μmoles/L of L-glutamate as sodium salt, 20 μmoles/L of L-aspartate as sodium salt and 400 μmoles/L of L-glutamine.

Co-enzyme Components:

Thiamine cocarboxylase plays an essential role in the oxidation of α-keto acids, and is included in the compositions to prevent the accumulation of pyruvate and pyruvate aldehyde and thereby cell toxicity.

In the tricarboxylic acid cycle, TPP is a co-factor in the metabolism of α-ketoglutaric acid to form succinyl-coenzyme A, by oxidative decarboxylation, or to form glutamate, by reductive amination.

In essence, TPP is involved in numerous interrelated, biochemical pathways, especially those of the Pentose Phosphate and Glycolytic pathways.

The thiamine may, for instance, be employed as thiamine pyrophosphate or as thiamine diamide.

Preferably the coenzyme component comprises 40.0 nmoles/L of thiamine as thiamine pyrophosphate chloride.

Vitaminoid Component

The vitaminoid, carnitine, has been reported to have multiple effects in improving cardiac function other than by simply optimising oxidative metabolism, such as, by promoting the utilization of alternative substrates and may additionally improve coronary blood flow. L-carnitine is preferred to the D- or DL-isomers, because it causes no inhibition of acetyl co-enzyme A/free fatty acid metabolism. Preferably the vitaminoid component comprises 50.0 μmoles/L of [-]-β-hydroxy-γ-trimethylamino-butyrate hydrochloride (L-carnitine). In this invention the inclusion of the L-isomer of carnitine in the formulation of the solution was intended to optimise the transport of long chain fatty acids from the cytosol into the mitochondrial matrix to the site of β-oxidation and thereby to buffer the intramitochondrial acetyl CoA/CoA ratio by stimulating the synthesis of acetyl carnitine from carnitine acetyltransferase. This reduction in the ratio of acetyl CoA/CoA will result in an efflux of acetyl carnitine from the mitochondria with an associated stimulation of pyruvate dehydrogenase and reversal of fatty acid inhibition of glucose oxidation. Ultimately, the optimisation of free fatty acid utilisation as an energy source is essential for all types of cells but this must be done with preservation of carbohydrate (glucose) utilisation by optimised functioning of the enzymes involved in glycolysis, eg. hexokinase, glucokinase, phosphofructokinase.

D- or DL-isomers of carnitine are less effective in fulfilling this function.

Insulin Components:

The use of human recombinant insulin (expressed in *E. Coli*) not only precludes the risk of antigenic or viral contamination in recipient cells/tissues/organs, as may be the case with insulin derived from other mammalian or animal species, but leads to a better fit being achieved of insulin molecules to human insulin receptor structure, ie. receptor specificity will be optimised to retain the many associated functions of insulin in cellular processes.

Preferably the protein component comprises 28.0 m. I.U./L of recombinant human insulin (expressed in *E. coli*).

Few of the disclosed formulations for perfusate and preservation solutions over the last 60 years having included insulin, and those that have, made use of insulin at unnatural levels, e.g. $10\text{–}50\times10^6$ mIU/L (i.e. about a million times more concentrated than in the compositions according to the invention). The reason for this relates to the fact that only a small amount of the insulin exists as single molecules in such concentrations. The rest of the insulin exists as large aggregates of insulin molecules which are ineffective in action, i.e. individual molecules of insulin are needed to stimulate insulin receptors on cell membranes.

Essentially, the biochemical effects of insulin do not simply relate to its ability to regulate carbohydrate metabolism and facilitated transport of circulating glucose into cells but also (i) the enhancement of intracellular glucokinase activity and amino-acid incorporation into proteins, (ii) stimulation of DNA translation, (iii) increased lipid synthesis, and (iv) stimulation of sodium, potassium and inorganic phosphate into cells.

The invention acknowledges that in the absence of species-specific insulin there will be profound changes in the entire balance of cellular metabolism, eg. increased gluconeogenesis from protein, increased lipolysis and ketogenesis. The net result will be a total disruption in metabolic homeostasis and cellular function.

The use of human recombinant insulin in the compositions according to the invention, in preference to animal serum-derived insulin, relates not only to meeting FDA regulations but to the fact that a better fit will be achieved of the insulin to the human insulin receptors, i.e. receptor specificity will be optimised.

Therefore, normal serum levels of insulin have been utilised in the compositions according to the invention and this could only be achieved by acidifying the insulin to prevent aggregates of insulin forming so allowing individual molecular species of insulin to exist in solution.

Using alkali or neutral pH solutions do not achieve this molecular dispersion of insulin molecules.

Antibiotic Components:

Preferably, an antibiotic component is included to ensure that, should there be any accidental contamination by micro-organisms during transport, any multiplication of such micro-organisms can be prevented. Preferably, the antibiotic component comprises 10 to 150 mg/L, more preferably 100 mg/L, of D-[-]-theo-2-dichloroacetamide-1-(p-nitrophenyl)-1,3-propane acid (chloramphenicol). Other antibiotics may be used, but care must be taken to ensure that the particular antibiotic employed does not interfere with the tissues or organs being stored or transported.

Ionic:

The concentrations of ionic species in solutions according to the invention acknowledges the activity coefficients of each ionic species and not simply their total serum concentrations. For instance, serum binding of $Ca^{2+}$ and $Mg^{2+}$ must be distinguished from the actual free, ionised levels of these ions. Magnesium ions are important in a number of critical cellular reactions and their extracellular presence is reported to stimulate mitochondrial respiratory activity and modulate the effects of rapid calcium influx and potassium efflux. Equally, an adequate concentration of calcium ions must be present in the preservation solution to avoid the calcium paradox, observed upon subsequent exposure of the donor organ to total serum calcium levels upon reperfusion and transplantation. Additionally, the ionic conductivity of solutions according to the invention is comparable to that of human serum, namely 12.6 mS cm$^{-1}$ and as such maintains the ionised status of the cell membrane and activities of enzymic moieties. Of significant concern in the majority of preservation solutions are the levels of potassium and sodium, in that the potassium ion concentration is some twenty-five times higher and sodium five to fifteen times lower than their serum levels.

Osmolarity:

A solution according to the invention is isosmotic to human serum (ca. 290 mOsmoles/L) and does not appear to necessitate the inclusion of plasma expanders, as demonstrated by the fact that only minor changes (ca. 8%) in hydration occur during long term (i.e. 4–52 h) hypothermic perfusion of the isolated rat heart and visceral nerve-muscle preparations. This may be explained by the fact that the cell membrane lies in continuity with a 99% gel interstitial phase so providing natural colloidal buffering to excess Donnan ionic equilibrium exchange across the cell membrane. The majority of the osmotic pressure is provided by Na$^+$ and its accompanying anions and only a small component (ca. 0.5%) can be attributed to plasma proteins and thereby has not justified the inclusion of oncotic agents in solutions according to the invention. The practicality of including oncotic agents, as in other commercially available perfusate/preservation solutions, is further compromised by their affinity for $Ca^{2+}$ and $Mg^{2+}$ necessitating prior dialysis in fresh solution so as not to disturb the cationic composition of the perfusate. The labile nature of polypeptide expanders also makes them impractical through their predisposition to mechanical denaturation as occurs in their preparation and circulation through perfusion apparatus. Unfortunately, while these colloidal expanders are essentially non-toxic, their use in preservation fluids is contraindicated in terms of, for example, (1) raised viscosity increases the thickness of the 'unstirred' layer around cells so hindering diffusion of metabolites, (2) alteration of the surface membrane bioelectric potential so disrupting cellular metabolism and receptor activities, (3) antigenicity of proteinaceous expanders, (4) agglutination and haemolysis of RBC's and (5) blockage of microvasculature and ischemia.

Amongst potential uses for the solutions according to the invention are as a flushing/holding/preserving/transporting medium for Human bone marrow cells at 4° C. (see Example 6) and Mammalian embryos (among others) for 12–48 hours at 20 to 37° C. (see Example 4). In agriculture this could be used for embryos of such species as sheep, goats, deer, cattle, pigs and horses.

Another potential use is as a non-frozen solution for use as a medium for storing semen for 24–48 hours at 20 to 25° C. The techniques heretofore used for this purpose are restricted solely to freezing the sperm with highly variable success. The solution is particularly useful for porcine semen since porcine semen cannot be frozen as compared to bovine semen.

In vitro applications in accommodating a variety of animal organ/tissue preparations used in physiological and pharmacological bioassay techniques for scientific experimentation at student to research levels of exploration, e.g.

a) perfused (cannulated)/perifused mouse, rat, guinea pig heart/heart-lung, liver, kidney preparations b) perifused visceral muscle preparations, e.g. blood vessels, G.I. tract, reproductive tract biopsies c) perifused mammalian skeletal muscle biopsies, e.g. mouse, rat, rabbit, human d) perfused tissue slices, e.g. liver, brain The preparation of solutions according to the invention is sensitive to the method by which stock solutions are prepared and stored, and to the order in which they are incorporated. The following Example is given as an instance of the preferred method of combining the various ingredients into the compositions.

EXAMPLE 1

Preparation of RS-I Solution

In the following, thiamine pyrophosphate (cocarboxylase), Sigma C4655 was prepared as a 0.4 mg/mL stock solution in MilliQ (endotoxin-free) purified water, and stored frozen in dark glass vials. Choline chloride (Sigma C7527) was prepared as a 17.5 mg/mL stock solution in MilliQ endotoxin-free purified water and stored frozen in glass vials. Human recombinant insulin (Sigma 10259) was prepared as a 0.5 I.U./mL stock solution in endotoxin-free MilliQ purified water acidified to pH 2.4 with 0.1N hydrochloric acid and stored frozen in glass vials.

In the following preparations, endotoxin-free MilliQ purified water was used throughout, both in the initial stirring, and in the final dilution.

For the preparation, a stainless steel container was filled with 8 litres of MilliQ and, the following ingredients were weighed out and added while constantly stirring, in the following order: 642.96 grams of sodium chloride (CFK0484), 37.28 grams of potassium chloride (BDH10198), 18.38 grams of calcium chloride dihydrate (BDS10117), 9.14 grams of magnesium chloride hexahydrate (BDH101494) and 106.61 grams of BES free acid (Sigma B6266), 1.84 milligrams of thiamine pyrophosphate (Sigma C9655) (using 4.6 mL of the stock solution), 0.9899 grams of L-carnitine (Sigma C0238), 0.1397 grams of choline chloride (Sigma 7527) in the form of 8 ml of the stock solution, 1.013 grams of glycerol (Sigma G2025), 2.8 I.U. of human recombinant insulin (5 ml of the stock solution), 0.310 grams of L-aspartate sodium salt (Sigma A6683), 180.2 grams of anhydrous D-glucose (Sigma G7021), 5.07 grams of L-glutamate sodium salt (Sigma G5889) and 5.84 grams of L-glutamine (Sigma G5763). The whole was stirred until completely dissolved and then the final volume of 10 litres was produced by adding further MilliQ purified water.

The solution was filtered through a sterile filter (0.2 μm Sartobran PH) into 100 mL sterile sealed glass bottles.

This solution is a 10×concentrate of the solution intended for use. When needed, it can be diluted with the appropriate quantity of MilliQ.

For use as a perfusion and preservation solution, 100 ml of the concentrate may be diluted with 900 mL of double deionised or endotoxin-free MilliQ purified water to 1 litre with the addition of 2.1 g of endotoxin-free sodium bicarbonate (Sigma S4019) and stored at 8–10° C. prior to use. Sodium bicarbonate is not added to the concentrates before they are stored, since extended storage of the concentrate containing bicarbonate ions may cause precipitations of calcium carbonate.

For use as a perfusion and preservation solution, each litre of solution may contain 100 mg/L of chloramphenicol (Sigma C3175) to prevent the risk of bacterial contamination as may occur during extended periods of in vitro experimentation under exposed, atmospheric conditions.

The following factors are very important in the preparation of compositions according to the invention. The most critical factors are:

1. The method of assembly of the solutions according to the invention and, specifically:
2. Use of endotoxin-free MilliQ water to make up all stock solutions and the 10×concentrate bottles of manufactured solutions according to the invention.
3. The method of preparing sterile stock solutions according to the invention and concentrates not involving autoclaving or irradiation—e.g. irradiation to achieve sterility resulted in degradation of glutamine and probably TPP.
4. The use of glass bottles for all storage of stock and 10×concentrates of solutions according to the invention.
5. Preparation of solubilised insulin by acidification at pH 2.4 plus storing insulin stock solutions frozen.
6. Preparation of thiamine pyrophosphate plus TPP stock solutions stored frozen under dark conditions (see reason below).
7. Preparation of choline-chloride plus stock solutions stored frozen.
8. Use of magnesium chloride hexahydrate (i.e. $6H_2O$). This is because if the dehydrate salt is used then as it adsorbs water the weight used to calculate the precise magnesium ion content will be in error—this is a common reason for wrongly made up Krebs solutions in terms of correct Mg-ion and Ca-ion levels.

It is not possible to omit any of the preferred components when formulating solutions according to the invention. All of these components work in synergy to produce the overall balanced physiological effect. This is why the use of human insulin and L-carnitine will only add to the overall attainment of viability of this versatile mammalian liquid medium.

Manufacture:

1. Stock solutions: Various stock concentrations of solutions according to the invention namely, 1×, 10× and 20× for long-term storage have been prepared and trialed successfully, but the preferred stock concentrates are 10× concentrates using endotoxin-free milliQ water and sterile filtered into sealed 100 mL bottles for storage under dark conditions at 3–8° C. Stock solutions are reconstituted for use as 1× concentrate solutions by the addition of 100 mL of 10× concentrates of stock solutions to 900 mL of double deionised or endotoxin-free MilliQ purified water with the addition of 2.1 g of sodium bicarbonate to give a final pH of 7.22±0.04 at 20° C. Sterile stock 10× concentrations of solutions according to the invention have a pH of 4.6±0.2 and have been shown to be retained as such for periods of up to five years. The recommended manufactured shelf-life of 10× stock concentrates of solutions according to the invention is 14 months when stored at 3–8° C.
2. Cocarboxylase: Stock solutions of thiamine pyrophosphate chloride (cocarboxylase) are prepared at 18.4 g/mL using endotoxin-free milliQ purified sterile filtered into dark sealed vials to prevent the photon degradation of thiamine pyrophosphate and stored frozen prior to the assemblage of 10× stock concentrates of solutions according to the invention.
3. Insulin: Human recombinant insulin is prepared as acidified (pH 2.4) stock concentrated solutions at 0.5 m I.U./mL using endotoxin-free milliQ purified water and sterile filtered into sealed vials and stored frozen prior to the assemblage of stock concentrates of solutions according to the invention.
4. Choline: Stock solutions of choline chloride are prepared at 17.45 mg/ML using endotoxin-free milliQ purified water and stored frozen in sealed vials prior to the assemblage of stock concentrates of solutions according to the invention.

5. Chloramphenicol is not an essential component of solutions according to the invention but is preferably added, either for storage, or after the storage vials have been opened, to ensure sterility during extended exposure of the solutions to the atmosphere, e.g. during perfusion or perifusion, or non-perfused preservation procedures.

The following further Examples show the use of solutions in accordance with the invention.

Figure 2:
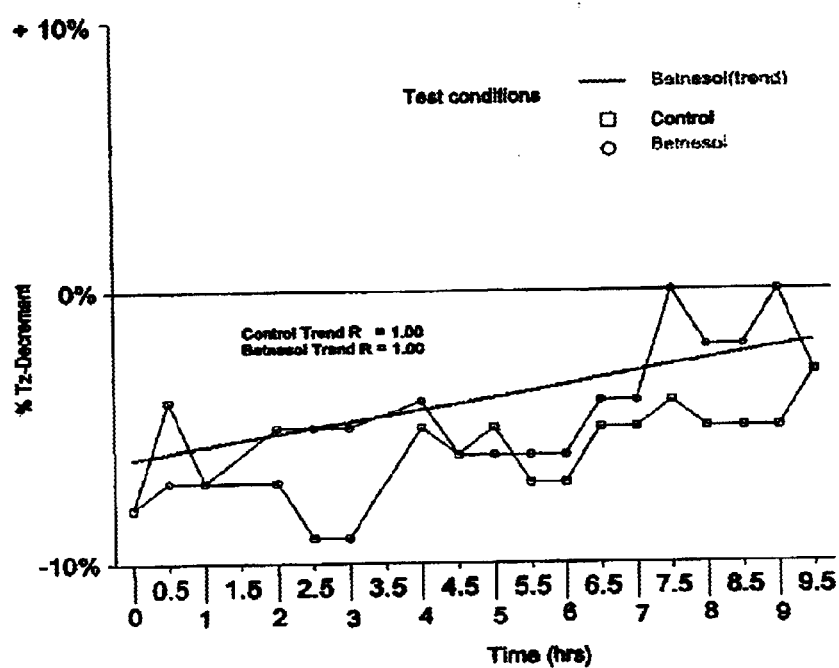
Figure 3:
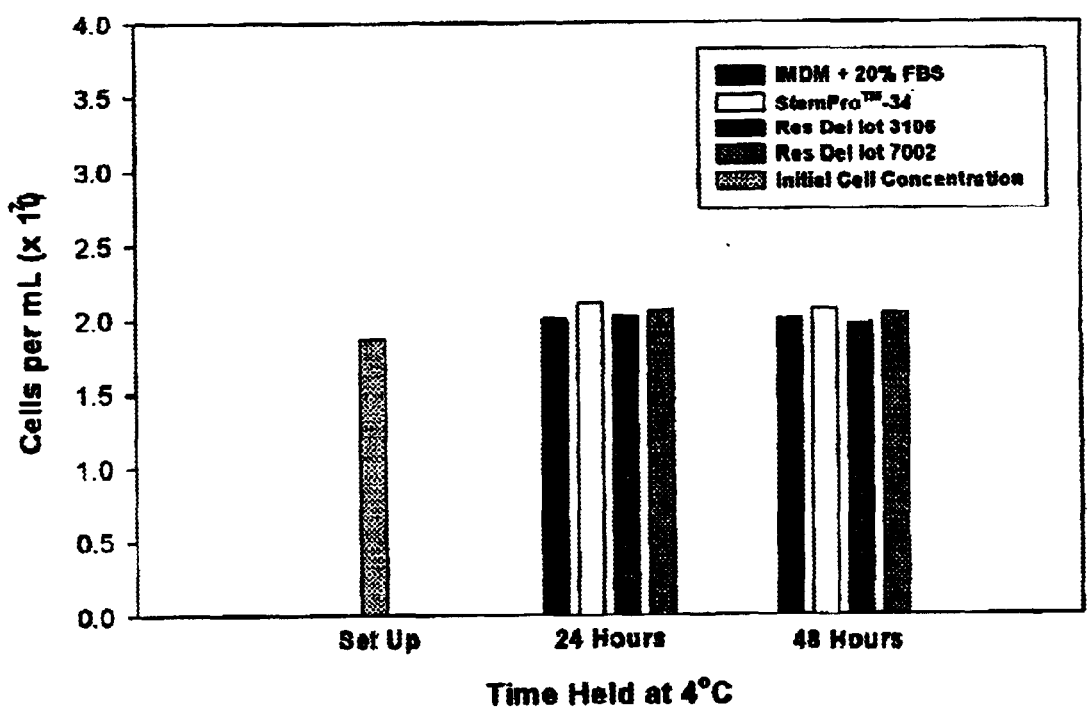
Figure 4:
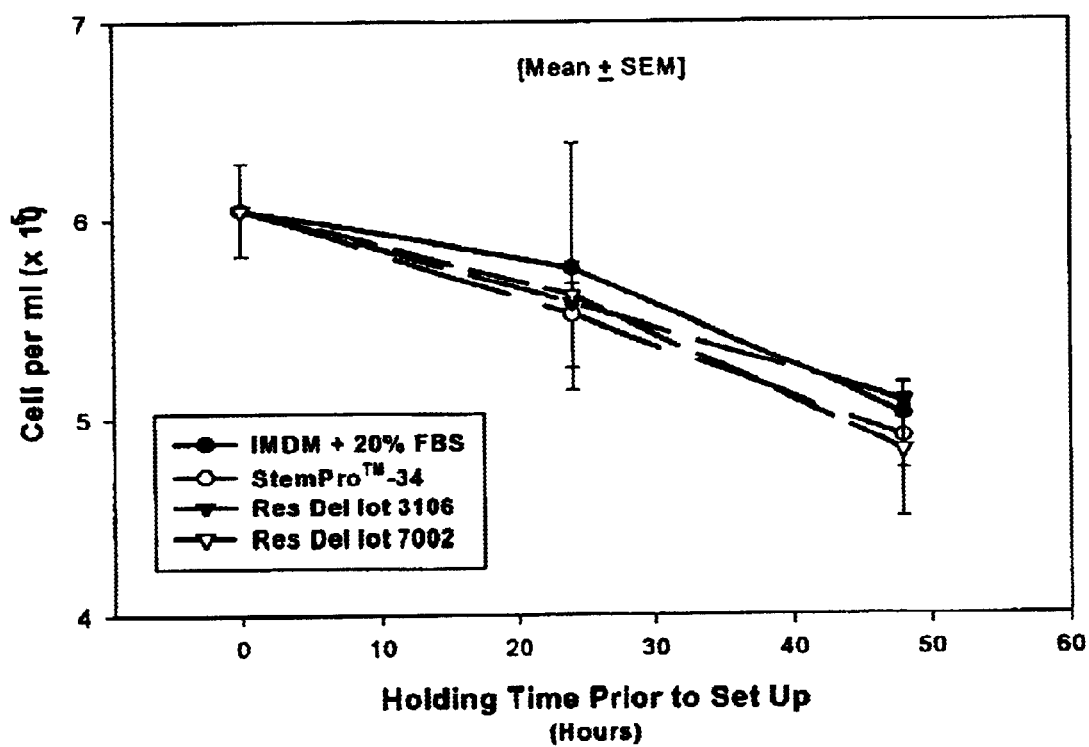

The accompanying drawings are graphs which are explained in the Examples, as follows:
FIG. 1 is a graph explained in Example 2;
FIG. 2 is a graph explained in Example 3; and
FIGS. 3 and 4 are graphs explained in Example 6.

EXAMPLE 2

Preservation of Physiological and Pharmacological Functions

A physiological medium according to the invention, prepared in accordance with Example 1, and hereinafter called RS-I solution, has been successfully used as a perfusion and preservation medium in physiological and pharmacological experiments, using a variety of different tissues and organs, isolated from a variety of mammalian species, including human biopsies.

The design of the formulation is based upon the chemical and physical composition of human serum which therein relates to its universal application and the results achieved to date (see Table 1).

The use of a non-phosphate buffer system to maintain stable pH values of isolated embryos (see Example 5) and human cells (see Example 6), and tissues/organs during storage at 3–10° C. or perfusion at 20–37° C. (Table 1) supports the contradictory use of conventional phosphate buffered media (Table 2).

This point has been validated in experiments designed to compare the adverse effects of phosphate buffered media (e.g. Krebs & Henseliet; Dulbecco) versus non-phosphate buffered RS-I solution (see Table 3). The use of phosphate buffered solutions is contraindicated in the storage of liver transplants based on the results achieved in isolated rat liver biopsies, where a significant loss of lactate dehydrogenase (LDH) was observed after only 10 minutes of perfusion with Krebs & Henseleit perfusate (FIG. 1). The addition of pyruvate to the perfusate (as proposed by others, e.g see WO 98/04127) to compensate for the inhibition of glycolysis by phosphate ions, is contraindicated, as pyruvate is known to cause inhibition of the $H_4$ and $H_3M$ subunits of LDH in the liver and would simply accentuate the observed deterioration.

TABLE 1

Functional viability of RS-I maintained mammalian tissue/organ preparations

|  |  | Max$^m$ Days | Preservation Conditions | |
| --- | --- | --- | --- | --- |
| Species | Tissue/Organ | Preparations | Stored in vitro ° C. | Exp. ° C. |
| rat | jejunum | 9.0 | 8–12 | 35 |
| " | " | 1.5 | — | 35 |
| " | ileum | 8.0 | 8–12 | 35 |
| " | " | 1.3 | — | 35 |
| " | colon | 5.0 | — | 20–35 |
| " | uterus | 3.0 | — | 35 |
| " | " | 10.0 | 8–12 | 35 |
| " | detrusor muscle | 2.0 | — | 20–35 |
| " | diaphragm muscle | 0.6 | — | 35–37 |
| " | " | 2.0 | — | 20–35 |
| " | soleus muscle | 1.1 | — | 20–35 |
| " | heart | 0.8 | — | 35–37 |
| " | " | 2.1 | — | 20–25 |
| " | heart-lung | 1.2 | — | 20–35 |
| " | RBC's | 4.0 | No haemolysis at 4° C. | |
| " | kidney | 1.0 | — | 20–35 |
| " | liver | 0.3 | — | 35 |
| rabbit | intestine | 5.0 | 8–12 | 37 |
| " | " | 2.0 | — | 20–37 |
| " | uterus | 7.0 | 8–12 | 37 |
| " | superior cervical ganglion | 2.0 | 8–12 | 37 |
| " | " | 0.8 | — | 37 |
| " | RBC's | 3.0 | No haemolysis at 4° C. | |
| guinea pig | ileum | 7.0 | 8–12 | 37 |
| " | detrusor muscle | 4.0 | 8–12 | 37 |
| " | " | 1.0 | — | 20–37 |
| " | heart | 0.4 | — | 20–37 |
| mouse | soleus | 0.9 | — | 20–35 |
| " | diaphragm | 1.5 | — | 20–35 |
| " | intercostal | 0.9 | — | 20–35 |
| " | diaphragm | 1.5 | — | 20–35 |
| human | intercostal | 1.3 | — | 37 |

(mepp discharge analysis applies to intercostal, diaphragm, intercostal rows)

TABLE 2

Comparative performances of isolated tissue/organ in RS-I solution versus conventional phosphate buffered solutions

| Species | Preparation Type | Experiment | Solution | °C. | Number | Time (hrs) | Survival % | Function % | RS-I Comparative % Performance of: Survival | Function |
|---|---|---|---|---|---|---|---|---|---|---|
| RAT | Vastus Lateralis | malignant hyperthermia clinical trials | RS-I | 35 | 12 | 8 | 80 | 90 | +800% | +150% |
|  |  |  | Krebs | 35 | 12 | 8 | 10 | 60 |  |  |
| RAT | Langendorff Heart | effect of RS-I and PS-I with | RS-I | 35 | 6 | 4 | 100 | 83 | +500% | +400% |
|  |  | phosphate buffer | | 35 | 16 | 4 | 20 | 20 |  |  |
|  |  | effect of mild hypothermia | RS-I | 15 | 5 | 24 | 90 | 65 | +900% | +550% |
|  |  | and conventional hypothermia | RS-I | 8 | 6 | 16 | 10 | 12 |  |  |
| RAT | Liver | retention of LDH | RS-I | 35 | 5 | 5 | 60 | 100 |  |  |
|  |  | with perfusion. | Krebs | 35 | 5 | 5 | 0 | 0 | (Krebs: total failure) |  |
| GOAT | Embryos | incubated in (a) | RS-I | 37 | 48 | >12 | 75 | 100 |  |  |
|  |  | vs. (b) | Dulbecco's | 37 | 55 | >12 | 13 | 100 | cf. (b) +570% | N/A |
|  |  | vs (c) | Whittingham's | 37 | 58 | >12 | 22 | 100 | cf. (c) +340% | N/A |

Attention is drawn to FIG. 1, a comparison of the lactate dehydrogenase (LDH) activity measured in perfusates from the isolated rat liver during perfusion/perifuision with RS-I solution (●-●) and Krebs-Henseleit saline (o----o) in a Res-Del® perfusion bath. An analysis of the time course of leakage of LDH using a repeated measure Anova programme indicates a highly significant ($p<0.001$) leakage of this intracellular enzyme from isolated rat liver preparations (n=5) maintained in K & H saline verses RS-I solution. Note that the leakage of Lactate Dehydrogenase (LDH) from preparations maintained in Krebs-Henseleit saline occurred within the first 10 minutes while LDH leakage in RS-I perfusates was not significant until 90 minutes and only showed a definite leakage after 240 minutes.

Each bar indicates standard error of the mean (SEM).

EXAMPLE 3

As a Diagnostic Solution for Drug Bioassay Evaluation

The standardised and stable composition of RS-I solution in terms of storage over time, a characteristic not found with conventional phosphate buffered solutions, ensures that the isolated preparations in each drug trial exhibit normal physiological responses in comparison to the decremental responsiveness observed in phosphate buffered solutions (e.g. Krebs & Henseleit, Tyrode's, Hank's salines).

In experiments designed to test the validity of using RS-I solution in preference to conventional Krebs & Henseleit saline on isolated rat diaphragm preparations, it was observed that after 1 hour of perfusion there was a 18.6% decrease in the neurally evoked twitch response compared to a 2.9% decrease in RS-I perfused preparations (Table 3).

This observation was further validated in experiments to demonstrate the potentiating effect of betamethasone (Betnesol®;Glaxo Ltd, NZ), on neurally evoked twitch responses in this preparation (Parr et al. British J. Anaesthesia, 67, 447–451; Robinson et al. Anesth. Analg. 74, 762–765) where it was imperative that the preparations should not exhibit any decrement in tetanic fade under 'control' conditions during experimental time periods, in order to validate the hypothesis that betamethasone had a potentiating effect of neurotransmitter release. Such was not found to be the case using Krebs and Henseliet saline even during the first 30 minutes of the experimental time period (see Table 3 and FIG. 2)

In another series of experiements, the classical guinea pig ileum preparation was trialed in RS-I solution and found to continue functioning and exhibiting normal pharmacological responses for up to 7 days. Such preparations have been alternatively stored in RS-1 solution at 8–10° C. and then successfully used in drug trials so saving the number of animals having to be sacrificed.

It is therefore believed that the validity of any drug bioassay responses recorded using a phosphate buffered solution as a diagnostic perfusate is seriously compromised by the deleterious effects previously reported to occur (Table 2).

TABLE 3

Twitch response data recorded from rat diaphragm preparations perfused with RS-I and Krebs & Henseleit solutions at 35° C.

|  | RS-I solution | | Krebs & Henseleit saline | |
|---|---|---|---|---|
| Time (min) | n | % Response‡ [mean ± SEM] | n | % Response‡ [mean ± SEM] |
| 30 | 8 | 0.2 ± 1.7 | 10 | 11.5 ± 2.7 |
| 60 | 8 | 2.9 ± 1.8 | 9 | 18.6 ± 2.7 |
| 90 | 8 | 7.0 ± 1.3 | 8 | 27.2 ± 4.3 |
| 120 | 8 | 10.2 ± 2.6 | 9 | 31.2 ± 3.8 |
| 150 | 8 | 14.9 ± 3.5 | 10 | 36.1 ± 3.7 |
| 180 | 7 | 18.8 ± 4.0 | 9 | 38.0 ± 3.6 |

‡Responses are expressed as the percentage twitch contraction at 30 minute intervals compared to the initial twitch contraction at time zero.

EXAMPLE 4

As a Cardioplegic Solution in Heart By-pass and Transplant Procedures

The advent of heart bypass and transplant surgery has accelerated the search for improved cardioplegic vehicles, because increasing the cardioplegic holding time will allow more involved cardiac surgery to be performed, without the present 45 minute time constraints.

Equally it would enlarge the donor pool area in terms of time and the current geographical restraints, and facilitate more efficient use of donor organs by overcoming tissue crossmatching in the recipient.

A cardioplegic solution may be used to serve two main purposes. Firstly in the situation of in vivo surgery, such as coronary bypass and valve replacement surgery, where the heart is stopped for a relatively short period (less than 45 minutes), with a combination of hypothermia (mild or extreme) and one of a number of cardioplegic solutions.

Secondly, a situation may exist for the use of a cardioplegic solution in the case of transplant surgery, whereby the heart is excised from the donor and transported in a cardioplegic preservation solution, RS-C, e.g. RS-I with 25.0 mmmoles/L of magnesium sulphate, to the recipient so as to preserve the metabolic status of the tissue.

The principal aims of a cardioplegic solution as summarised by Buckberg (J. Thoracic Cardiovasc. Surg. 77, 803–815) are to:

protect the myocardium from the deleterious effects of ischaemia.
reduce the energy requirements of the muscle, but provide an environment where energy production continues.
arrest the heart safely.

A cardioplegic solution must fulfil these aims as well as prevent the negative effects of acidosis and oedema and stabilise the membrane to prevent unnecessary loss of intracellular ions.

In this study a horizontally aligned version of the Langendorff heart preparation was isolated in a Res-Del® 589 Perfusion Bath System and used to assess the viability of cardioplegic RS-C. The modified Langendorff preparation used, enabled simultaneous measurements of the heart rate and isovolumetric changes in the preparation, via an on-line pressure transducer. Coronary flow rates and an analysis of the electrocardiographic activity were also measured.

The cardioplegic techniques employed was either one of continuous infusion of the cardioplegic solution in the retrograde direction or, as conventionally practiced in heart by-pass surgery, a 'single' opposed bolus injection of the cardioplegic solution. The supposition was made that a continuous infusion would preclude the development of ischaemia or hypoxia during cardioplegic episodes. The results achieved in Tables 4–6 indicated that a 100% preservation of functional activity in the arrested hearts had been achieved for periods of up to six hours over a temperature range of 20–35° C.

Interestingly, the percentage recovery did not appear to depend on coronary flow rates which were negative in experiments conducted over 3–6 hours.

TABLE 4

Effect of perfused RS-C solution on the Res-Del ® Langendorff rat preparation

| HEART Nos. | CP-PERIOD (hr) | CFR % CHANGE DURING CP | % RECOVERY WD @ 5 min | % RECOVERY WD @ 40 min | CFR % CHANGE @ 40 min |
|---|---|---|---|---|---|
| 6 | 1 | +3 | +83 | +22 | −12 |
| 6 | 3 | −40 | +68 | −7 | −46 |
| 6 | 6 | −49 | −20 | +5 | −56 |

TABLE 5

Average times to cessation and recovery of 'cardiolplegic' Res-Del ® Langendorff rat heart preparations

| | 1 hour CP-PERIOD | | 3 hour CP-PERIOD | | 6 hour CP-PERIOD | |
|---|---|---|---|---|---|---|
| HEART Nos. | STOP | START | STOP | START | STOP | START |
| 6 | 34 | 142 | 25 | 93 | 44 | 91 |

TABLE 6

Effect of 'Single' bolus RS-C solutions on the Res-Del ® Working rat heart preparation

| HEART Nos. | CP-PERIOD | % RECOVERY WD @ 10 min | % RECOVERY WD @ 40 min | CFR % CHANGE @ 40 min |
|---|---|---|---|---|
| 4 | 1 | +1 | +18 | −56 |
| 4 | 3 | +33 | +21 | −40 |

EXAMPLE 5

As a 'Flush' and 'Hold' Solution in Animal Embryo Transplant Procedures

In independent trials, RS-I solution was trialed as a 'flush', 'hold' and incubation medium for Mammalian embryos (among others) against commercially available phosphate buffered media over 12–18 hours.

In these experiments goat embryo were incubated in Dulbecco's, Whittingham's and RS-I media at 38° C. for 12–18 hours to assess survival rate.

The results indicated that RS-I solution offered superior preservation (75%) in comparison to Dulbecco's (24%) and Whittingham's (38%) for medium to long-term incubation of embryos (Table 7).

In another independent study conducted on cattle embryos, the selection of the Good's buffer, BES, was assessed in comparison to the Good's buffers, HEPES and MOPS and conventional phosphate buffering solution, PBI.

These results indicate that only in RS-I/BES buffered solution did the embryos show any improvement in development (Table 8) even though compromised by initial incubation in PBI solution and an anticipated inhibition of their metabolic status (ref. Table. 2).

TABLE 7

Comparative study on RS-I solution as a medium for goat embryo preservation

| TRIAL | EMBRYO NUMBERS[a] | | |
|---|---|---|---|
| MEDIUM | 'SURVIVED' | 'DEGENERATE' | TOTALS |
| Dulbecco's PBS + 10% goat serum | 13 (24%) | 42 (76%) | 55 |
| Whittingham's + 10% goat serum | 22 (38%) | 36 (62%) | 58 |
| RS-I solution | 36 (75%) | 12 (25%) | 48 |

[a]Embryos were incubated 12–18 hours at 38° C. with 100% humidity

TABLE 8

Assessment of RS-I [BES], HEPES-HOLD, MOPS-HOLD and PBI-HOLD solutions as a culture medium for cattle embryo

| Medium | N | % Poorer | % Same | % Improved |
|---|---|---|---|---|
| HEPES/HOLD | 12 | 17 | 75 | 8 |
| MOPS/HOLD | 13 | 8 | 92 | 0 |
| BES/RS-I HOLD | 15 | 40 | 40 | 20 |
| PBI-HOLD | 15 | 27 | 73 | 0 |

The RS-I results in these trials were compromised because ALL cattle embryos were 'flushed' and 'held' in BSA-enriched phosphate solution (FBI) for up to 6 hours prior to experimentation in the different types of Good's buffered media.

The additional use of RS-I in such applications in embryo preservation during 'hold phases' resides in the fact that it has proved to be equally effective under mild hypothermic conditions in terms of cell, tissue and organ preservation.

EXAMPLE 6

As a 'Holding' Media for Human Normal Bone Marrow

In independent trials conducted at Life Technologies Inc. N.Y, USA, RS-I solution was assessed against conventional serum supplemented or serum free media formulations as a holding medium for the temporary storage of freshly harvested human bone marrow cells.

The experimental procedures involved mixing one mL of bone marrow with one mL of the following test media:
MDM+20% FBS
StemPro™-34 without recombinant growth factors
RS-I/Res-Del media lot 3106
RS-I/Res-Del media lot 7002

The samples of media and marrow were then placed at 4° C. Aliquots of the marrow were stained with antibodies for flow cytometric analysis.

Additional aliquots of the bone marrow were seeded into StemPro™-34 supplemented with the human recombinant growth factors: Stem Cell Factor (100 ng/mL), IL-3 (50 ng/mL) and GM-CSF (25 ng/mL). The cells were incubated for six days at 37° C. in a humidified atmosphere of 5% $CO_2$ and air.

After storage at 4° C. for 24 and 48 hours, aliquots of the bone marrow in the indicated media were taken for cell counts and viability as described above. Aliquots were also stained for flow cytometric analysis and ex vivo cell expansion as described.

During the time course of this study, cell viability as determined by Trypan Blue dye exclusion, remained essentially 100% for the bone marrow cells, irrespective of the media formulation. During storage at 4° C. there was a slight but not significant increase in cell number in all of the formulations tested (see FIG. 3).

The proliferative potential of the progenitor cells in the bone marrow by culturing aliquots of the marrow in StemPro™-34 supplemented with a combination of human recombinant growth factors demonstrated to promote cell expansion.

Aliquots of the bone marrow cells stored in the various media formulation tested were cultured in StemPro-34 supplemented with the human recombinant growth factors SCF (100 ng/mL), IL-3 (50 ng/mL) and GM-CSF (25 ng/mL). The cells were grown for 6 days and then cells counts determined using a Coulter Counter.

All of the media formulations tested showed a similar decline in the proliferation of the progenitors cells after 24 and 48 hours storage at (FIG. 4).

It was concluded that RS-I solution could be used as an alternative to phosphate buffered media to circumvent the published deleterious effects on isolated mammalian cells, tissues and organs (See Table 2).

What is claimed is:

1. A physiological medium which comprises an aqueous solution in sterile purified water of:
   (i) a salt component comprising:
   (a) from 100 to 150 mmoles/L of sodium ions,
   (b) from 2.5 to 6.2 mmoles/L of potassium ions,
   (c) from 0.1 to 2.5 mmoles/L of calcium ions,
   (d) from 0.4 to 25 mmoles/L of magnesium ions, and
   (e) from 96 to 126 mmoles/L of chloride ions;
   (ii) a buffer component comprising
   (f) from 21 to 27 mmoles/L of bicarbonate ions, and
   (g) from 1 to 12 mmoles/L of TES, MOPS or BES;
   (iii) a substrate component comprising:
   (h) 2 to 11 mmoles/L of glucose
   (i) 50 to 150 μmoles/L of glycerol and
   (j) 7 to 15 μmoles/L of choline;
   (iv) an amino acid component comprising:
   (k) 5 to 400 μmoles/L of glutamate,
   (l) 5 to 200 μmoles/L of aspartate and
   (m) 100 to 2000 μmoles/L of glutamine;
   (v) a co-enzyme component comprising:
   (n) 1 to 120 nmoles/L of thiamine pyrophosphate;
   (vi) a vitaminoid component comprising:
   (o) 40 to 70 μmoles/L of D- or DL- or L-carnitine;
   (vii) a protein component comprising:
   (p) 5 to 200 m I.U./L of porcine or human insulin.

2. The physiological medium as claimed in claim 1 which further comprises
   (viii) an antibiotic component comprising:
   (q) 10 to 150 mg/L of chloramphenicol.

3. The physiological medium as claimed in claim 1 wherein the salt component comprises:
   (c) from 1.0 to 2.5 mmoles/L of calcium ions, and
   (d) from 0.4 to 2.4 mmoles/L of magnesium ions.

4. The physiological medium as claimed in claim 1 wherein the salt component comprises
   135.32 mmoles IL of sodium ions, 5.00 mmoles/L of potassium ions, 1.25 mmoles/L of calcium ions, 0.45 mmoles/L of magnesium ions, and 118.40 mmoles/L of chloride ions as sodium, potassium, calcium and magnesium salts.

5. The physiological medium as claimed in claim 1 wherein the buffer component comprises 25.00 mmoles/L of bicarbonate ions as sodium salt and 5.0 mmoles/L of N,N-bis (2-hydroxy ethyl)-2-amino-ethanesulfonic acid (BES).

6. The physiological medium as claimed in claim 1 wherein the substrate component comprises 10 mmoles/L of D-glucose, 110 μmoles/L of glycerol and 10.0 μmoles/L of choline as the chloride salt.

7. The physiological medium claimed in claim 1 wherein the amino acid component comprises 300 μmoles/L of L-glutamate as sodium salt, 20 μmoles/L of L-aspartate as sodium salt and 400 μmoles/L of L-glutamine.

8. The physiological medium claimed in claim 1 wherein the co-enzyme component comprises 40.0 nmoles/L of thiamine as thiamine pyrophosphate.

9. The physiological medium as claimed in claim 1 wherein the vitaminoid component comprises 50.0 μmoles/L of -p-hydroxy-γ-trimethylaminobutyrate hydrochloride (L-carnitine).

10. The physiological medium as claimed in claim 1 wherein the protein component comprises 28.0 m. I.U./L of recombinant human insulin.

11. The physiological medium as claimed in claim 1 wherein the antibiotic component comprises 100 mg/L of D-theo-2-dichloroacetamide-I-(p-nitrophenyl)-1,3-propane acid (chloramphenicol).

12. The method for producing a physiological medium according to claim 1 which comprises adding in the following order: sodium chloride, potassium chloride, calcium chloride, magnesium chloride, the TES, MOPS, or BES, thiamine pyrophosphate, carnitine, choline, glycerol, insulin, aspartate, glucose, glutamate, glutarnine, and sodium bicarbonate to sterile purified water, with constant stirring, making up to the desired volume, filtering and storing in sterile sealed vessels.

13. The concentrates for the preparation of a physiological medium as claimed in claim 1 which comprise the salt, buffer, substrate, amino acid, co-enzyme, vitaminoid and protein components, and dilutable with sterile purified water to form said physiological medium.

14. The concentrates for the preparation of a physiological medium as claimed in claim 1 which comprise the salt, buffer, substrate, amino acid, co-enzyme, vitaminoid and protein components, except for sodium bicarbonate, and dilutable with sterile purified water with the addition of sodium bicarbonate to form said physiological medium.

15. The physiological medium as claimed in claim 10 wherein the recombinant human insulin derived from expression in *E.coli*.

* * * * *